(12) United States Patent
Liu (10) Patent No.: US 9,221,862 B2
(45) Date of Patent: Dec. 29, 2015

(54) ERYTHROMYCIN ETHYLSUCCINATE CRYSTALLINE HYDRATE, PREPARATION AND USES THEREOF

(76) Inventor: Li Liu, Foshan (CN)

( * ) Notice: Subject to any disclaimer, the term of this patent is extended or adjusted under 35 U.S.C. 154(b) by 4 days.

(21) Appl. No.: 14/113,182

(22) PCT Filed: Apr. 20, 2012

(86) PCT No.: PCT/CN2012/074423
§ 371 (c)(1),
(2), (4) Date: Dec. 31, 2013

(87) PCT Pub. No.: WO2012/142960
PCT Pub. Date: Oct. 26, 2012

(65) Prior Publication Data
US 2014/0128583 A1    May 8, 2014

(30) Foreign Application Priority Data

Apr. 21, 2011  (CN) .......................... 2011 1 0101180

(51) Int. Cl.
| | |
|---|---|
| *A61K 31/70* | (2006.01) |
| *C07H 17/08* | (2006.01) |
| *C07C 19/03* | (2006.01) |
| *C07C 31/08* | (2006.01) |
| *C07C 31/10* | (2006.01) |
| *C07C 43/06* | (2006.01) |
| *C07C 49/08* | (2006.01) |
| *C07C 69/14* | (2006.01) |
| *C07C 255/03* | (2006.01) |
| *C07D 307/06* | (2006.01) |
| *A61K 31/7048* | (2006.01) |
| *C07D 407/14* | (2006.01) |

(52) U.S. Cl.
CPC ............ *C07H 17/08* (2013.01); *A61K 31/7048* (2013.01); *C07C 19/03* (2013.01); *C07C 31/08* (2013.01); *C07C 31/10* (2013.01); *C07C 43/06* (2013.01); *C07C 49/08* (2013.01); *C07C 69/14* (2013.01); *C07C 255/03* (2013.01); *C07D 307/06* (2013.01); *C07D 407/14* (2013.01)

(58) Field of Classification Search
CPC ....................................................... C07H 17/08
See application file for complete search history.

(56) References Cited

U.S. PATENT DOCUMENTS 5,118,799 A    6/1992    Rossignol

FOREIGN PATENT DOCUMENTS

| CN | 1098106 A | 2/1995 |
|---|---|---|
| CN | 1602887 A | 4/2005 |

OTHER PUBLICATIONS

International Search Report mailed Aug. 9, 2012 (PCT/CN2012/074423); ISA/CN.
Zhang, T. et al : Development of Taste Making Methods in Oral Pharmaceuticals, Hebei Chemical Engineering and Industry, 30(11), Nov. 2007, pp. 20-22, 25.
Zhang, T. et al. : Development of Taste Making Methods in Oral Pharmaceuticals, Hebei Chemical Engineering and Industry, 30(11), Nov. 2007, pp. 20-22, 25.
Package Insert of erythromycin ethylsuccinate copied from http://www.rxlist.com/erythromycin-ethylsuccinate-drug.htm) (see <http://www.rxlist.com/erythromycin-ethylsuccinate-drug.htm>), Last reviewed on RxList: Feb. 11, 2009, Copyright © 2015 by RxList Inc.

*Primary Examiner* — Elli Peselev
(74) *Attorney, Agent, or Firm* — Banner & Witcoff, Ltd.

(57) ABSTRACT

An anti-infective drug-macrolide derivate, preparation and uses thereof. Macrolide derivate, namely erythromycin ethylsuccinate crystalline hydrate. Preparation of erythromycin ethylsuccinate crystalline hydrate medicaments for the treatment and prevention of human or animal infectious diseases caused by Gram-positive or negative bacteria.

11 Claims, 4 Drawing Sheets

ERYTHROMYCIN ETHYLSUCCINATE CRYSTALLINE HYDRATE, PREPARATION AND USES THEREOF

The present application is a U.S. National Phase filing of International Application No. PCT/CN2012/074423, filed on Apr. 20, 2012, designating the United States of America and claiming priority to and the benefit of Chinese Application No. 201110101180.9, filed on Apr. 21, 2011. The present application claims priority to and the benefit of the above-identified applications, and the above-identified applications are incorporated by reference herein in their entirety.

TECHNICAL FIELD

The present invention relates to the field of medical technology, particularly provides anti-infective drugs-erythromycin ethylsuccinate crystalline hydrates, and the preparation and use thereof.

BACKGROUND ART

It has only been reported in the literature: erythromycin ethylsuccinate [$C_{43}H_{76}NO_{16}$, with a molecular weight of 862.07, CAS No.: 1264-62-6], and its use. So far, there is no report in the literature concerning macrolide derivatives-erythromycin ethylsuccinate crystalline hydrates [$C_{43}H_{75}NO_{16} \cdot nH_2O$, n=0.2 to 0.6, and the preparation method and use thereof.

SUMMARY OF THE INVENTION

Technical Problem

The present invention relates to the hydrate of an anti-infective drug-macrolide derivative—erythromycin ethylsuccinate (CAS No.: 1264-62-6) and the use and preparation thereof. The erythromycin ethylsuccinate crystalline hydrate according to the present invention has a general formula of $C_{43}H_{75}NO_{16} \cdot nH_2O$, n=0.2 to 0.6, n can be 0.25, 0.5 as well as a number therebetween. The erythromycin ethylsuccinate crystalline hydrate according to the present invention has different crystalline form, but in any case, the characteristic thermogram of the hydrates of the present invention exhibits distinct endothermic peak (TG-DTA or TG-DSC). These crystalline hydrates have not been reported in the world.

Technical Solution

The process for preparing erythromycin ethylsuccinate hydrate comprises: method A. in a reaction vessel, one or more of a $C_1$-$C_6$ lower alcohol, a $C_2$-$C_6$ lower nitrile, a $C_3$-$C_8$ lower ketone or $C_2$-$C_8$ lower ether is used as a solvent, to the solvent is added erythromycin, stirred at a temperature of 0-50° C. to dissolve erythromycin; to the solution is added sodium bicarbonate or sodium carbonate or potassium carbonate, and water, stirred, and cooled to 20° C. or below; to the cooled mixture is added monoethyl succinate halide, including monoethyl succinate chloride or monoethyl succinate bromide, allowed to react, and monitored by TLC until the reaction is complete; to the resultant is added an acid or a base to control the pH value at about 7.0-8.5; the organic phase is precipitated and separated; to the organic phase is added water, cooled to −20° C.-10° C.; upon the solid is precipitated completely, the mixture is filtered, the resulting solid is recrystalized with water and one or more of a $C_1$-$C_6$ lower alcohol, a $C_2$-$C_6$ lower nitrile, a $C_2$-$C_8$ lower ether, a $C_3$-$C_8$ lower ketone or $C_1$-$C_6$ lower halogenated hydrocarbons as solvent once or more times, cooled to −20° C.-10° C., filtered, dried to obtain erythromycin ethylsuccinate crystalline hydrate;

or method B: in a reaction vessel, one or more of a $C_1$-$C_6$ lower alcohol, a $C_2$-$C_6$ lower nitrile, a $C_3$-$C_8$ lower ketone or $C_2$-$C_8$ lower ether is used as a solvent, to the solvent is added one or more of erythromycin thiocyanate or erythromycin thiocyanate hydrate, erythromycin lactate, stirred, added sodium bicarbonate or sodium carbonate or potassium carbonate, and water, allowed to react with stirring for 1-3 hours, added dropwise an aqueous solution of an acid or a base, stirred to control the pH value at about 7.0-8.5; the organic phase is precipitated and separated; to the organic phase is added sodium bicarbonate or sodium carbonate or potassium carbonate, and water, stirred, cooled to 20° C. or below, added monoethyl succinate halide, including monoethyl succinate chloride or monoethyl succinate bromide, allowed to react, monitored by TLC until the reaction is complete; to the resultant is added an acid or a base to control the pH value at about 7.0-8.5; the organic phase is precipitated and separated; to the organic phase is added water, cooled to −20° C.-10° C., upon the solid is precipitated completely, the mixture is filtered, the resulting solid is recrystalized with water and one or more of a $C_1$-$C_6$ lower alcohol, a $C_2$-$C_6$ lower nitrile, a $C_2$-$C_8$ lower ether, a $C_3$-$C_8$ lower ketone or $C_1$-$C_6$ lower halogenated hydrocarbons as solvent once or more times, cooled to −20° C.-10° C., filtered, dried to obtain erythromycin ethylsuccinate crystalline hydrate.

The recrystallization in the process can be carried out repeatedly, which facilitates the obtainment of the higher purity product of the present invention. Erythromycin ethylsuccinate crystalline hydrate can be obtained under different preparation conditions, especially under different drying temperature conditions.

The solvent for the crystallization or recrystallization of erythromycin ethylsuccinate crystalline hydrate is preferably selected from the group consisting of water, methanol, ethanol, isopropanol, acetonitrile, diethyl ether, tetrahydrofuran, acetone, hexone, methylene chloride, chloroform and ethyl acetate.

According to the present invention, the lower alcohol or low molecular weight alcohol has 1-6 carbon atoms (i.e. an alcohol having 1-6 carbon atoms), such as methanol, ethanol, isopropanol, butanol, and the like; $C_2$-$C_6$ lower nitrile has 2-6 carbon atoms, such as acetonitrile, propionitrile, etc.; $C_2$-$C_8$ lower ether or low molecular weight ether has 2-8 carbon atoms, such as diethyl ether, diisopropyl ether, dibutyl ether, etc.; the lower halogenated hydrocarbon has 1-6 carbon atoms, including dichloromethane, dichloroethane, chloroform, etc.; the lower ester has 2-8 carbon atoms, including butyl acetate, ethyl acetate, ethyl formate, etc.; the low molecular weight straight or branched alkane or cycloalkane has 5-10 carbon atoms, including pentane, n-hexane, cyclohexane, petroleum ether, etc.; the low molecular weight aromatic hydrocarbon has 6-12 carbon atoms, including benzene, toluene, etc.; the $C_3$-$C_8$ low molecular weight ketone has 3-8 carbon atoms, including acetone, butanone, pentanone, hexanone, hexone; the $C_1$-$C_6$ low molecular weight acid is an organic acid having 1-6 carbon atoms, including formic acid, acetic acid, propionic acid, etc.; regarding marking method of the number of carbon atoms of any class of compounds described as "low molecular weight", as long as they appear once in the text of the present application, the number of carbon atoms of any compound of same class described as "low molecular weight" which is not marked are consistent with number of carbon atoms marked in the present application.

In the present invention, the moisture content is determined by Karl Fischer method with 10% imidazol in anhydrous methanol as a solvent. For eliminating the effect of erythromycin and monoethyl succinate on moisture content determination during Karl Fischer determination, erythromycin reference and monoethyl succinate reference can be employed. In the present application, the melting point of erythromycin ethylsuccinate crystalline hydrate at different times is measured using a melting point apparatus, and the melting point apparatus is not corrected.

The samples of the present invention were determined according to identification items (1) and (2) of erythromycin ethylsuccinate in Chinese Pharmacopoeia CP2005 version. The results comply with corresponding provisions.

Powder X-ray diffraction is typically used to characterize and/or identify polymorphic forms. When powder X-ray diffraction is used to characterize and/or identify polymorphic forms, 'about' is used before the peak value. In view of inherent change in the peak value, it is usual practice in the field of solid-state chemistry. The accuracy of powder spectrum peak 2θ x-axis value is usually at ±0.2° 2θ level. Therefore, a powder X-ray diffraction peak appearing at about 8.0° 2θ means that, when measured on most X-ray diffractometer, peak may be between 7.8° 2θ and 8.2° 2θ. The variation of peak intensity depends on how each crystal orientates in the sample container with respect to external X-ray source; the orientation effect does not provide structural information about the crystal.

In one aspect, the present invention provides different crystalline hydrates of erythromycin ethylsuccinate.

In another aspect, the present invention provides different crystalline forms of crystalline hydrates and their preparation process.

In another aspect, the present invention provides a pharmaceutical composition comprising one or more erythromycin ethylsuccinate crystalline hydrates prepared by the method of the present invention, and one or more pharmaceutically acceptable excipients.

The present invention further provides a method for the preparation of pharmaceutical formulations, comprising combining one or more erythromycin ethylsuccinate crystalline hydrates prepared by the method of the present invention and at least one pharmaceutically acceptable excipient.

The present invention further provides use of erythromycin ethylsuccinate crystalline hydrates and different crystalline form of crystalline hydrates, such as erythromycin ethylsuccinate 0.5 $H_2O$ hydrate, 0.25 $H_2O$ hydrate, etc. for the preparation of a pharmaceutical composition for the treatment of infections, including bacterial infections, Gram-positive and or Gram-negative bacterial infections, mycoplasma, chlamydia infection.

The erythromycin ethylsuccinate crystalline hydrate of the present invention may be used for preparing solid formulations, including tablets, capsules, granules, effervescent tablets, ointments and gels by the administration to the skin, vaginal gels, and suppositories by vaginal or rectal administration, and the like.

When used for preparing solid formulations, such as tablets, capsules, granules, effervescent tablets, the formulations can contain pharmaceutically acceptable fillers, such as starch, modified starch, lactose, microcrystalline cellulose, cyclodextrin, sorbitol, mannitol, calcium phosphate, amino acids, etc.; pharmaceutically acceptable disintegrants, such as starch, modified starch, microcrystalline cellulose, sodium carboxymethyl starch, crosslinked polyvinylpyrrolidone, low substituted hydroxypropyl cellulose, surface active agents; pharmaceutically acceptable wetting agent and a binder, such as gelatinised starch, methyl cellulose, sodium carboxymethyl cellulose, ethyl cellulose, polyvinylpyrrolidone, alginic acid and salts thereof; pharmaceutically acceptable lubricant and a glidant, such as stearic acid, magnesium stearate, polyethylene glycol 4000 to 8000, talc, aerosil, magnesium lauryl sulfate, etc.; and pharmaceutically acceptable sweeteners and flavors, such as aspartame, sodium cyclamate, sodium saccharin, sucralose, edible essence.

The composition for preparing a tablet or capsule filler can be prepared by wet granulation. During wet granulation, some or all of the active ingredients or excipients in powder form are mixed, and then further mixed in the presence of liquid, which makes the powder agglomerate into particles. The particles were sieved or ground, dried, and sieved to obtain desired particle size. The particles may then be tableted, or added with other excipients such as glidants and/or lubricants before preparation.

The compositions prepared into tablets can be prepared by dry mixing. For example, the composition of a mixture of active ingredient and excipient can be compacted as small pieces or flakes, and then comminuted into compacted granules, and the compacted granules can then be compacted into tablets.

As an alternative of dry granulation method, the mixed composition may be directly dry tableted. Directly tabletting results in more uniform tablets. Excipients particularly suitable for direct tabletting include microcrystalline cellulose, spray-dried lactose calcium phosphate and colloidal silica. The proper use of these excipients and other excipients in direct tabletting is well known by those skilled in the art having experiences and skills.

The capsule filler of the present invention can contain any of the above mixture and the particles or granules, prepared as described into Reference tablet, but they are not subjected to the last step of the mixture into a tablet.

The preparation of suppository of erythromycin ethylsuccinate crystalline hydrate: erythromycin ethylsuccinate crystalline hydrate 1 to 50%, suppository matrix 50 to 99%; the matrix may be one or more of ethanol, glycerol, glycogelatin, polyethylene glycol 200 to 8000, poloxamer, semi-synthetic stearates, Carbomer series (931, 934, 940, 974, AA-1, 1342, etc.), Tween 60 to 80. The process comprises: mixing the agents and matrix, heating them in water bath, stirring, melting, stirring until they are uniform, and quickly pouring them into a suppository mold coated with a lubricant to slightly overflow suppository mode, cooling, leveling, and drawing.

The preparation of ointment and gel of erythromycin ethylsuccinate crystalline hydrate: erythromycin ethylsuccinate crystalline hydrate (based on erythromycin, feeding) is mixed with 50 to 99% matrix; the matrix may be one or more of ethanol, glycerol, triethanolamine, glycogelatin, polyethylene glycol 200 to 8000, poloxamer, polyvinylpyrrolidone, semi-synthetic stearates, water-soluble monoglyceride, petrolatum, carbomer series (931, 934, 940, 974, AA-1, 1342, etc.), Tween 60 to 80. The suppository may contain pharmaceutically acceptable preservatives and stabilizers. In the preparation, carbomer is dispersed with water, and then glycerin, polyethylene glycol 200 to 8000 are added, heated in water bath, stirred and mixed; erythromycin ethylsuccinate crystalline hydrate in prescribed amount is added, stirred, the pH is adjusted with a pharmaceutically acceptable inorganic base or organic base to 5.0 to about 7.5, and then water is added to the whole amount, stirred until uniform, and packaged.

The clinical applications of erythromycin ethylsuccinate hydrate of the present invention:
Anti-infective drugs—macrolide derivative—erythromycin ethylsuccinate crystalline hydrates of the present invention have broad-spectrum antibacterial effect, and are suitable for the preparation of a medicament for the treatment and prevention of infections in human and animal caused by erythromycin-sensitive susceptible strains, *Mycoplasma, Chlamydia*, including: 1. Acute tonsillitis, acute pharyngitis, sinusitis; scarlet fever, cellulitis, diphtheria and diphtheria carriers, gas gangrene, anthrax, tetanus, actinomycosis, syphilis, *Listeria monocytogenes* disease, 2. Legionnaires' disease, 3. *Mycoplasma pneumoniae* pneumonia, 4. *Chlamydia pneumoniae* pneumonia, 5. genitourinary infection caused by other *Chlamydia, Mycoplasma*, 6. *Chlamydia trachomatis* conjunctivitis, 7. Oral infections caused by anaerobic bacteria, 8. *Campylobacter jejuni* enteritis, 9. Whooping cough, 10. Recurrence of rheumatic fever, infective endocarditis, or oral and upper respiratory medical procedures.

Solution of the Present Invention

Usage and dosage: under normal circumstances, parenteral administration (based on erythromycin), adult: 0.75-2 g, 3 to 4 times a day; for children weighing 20 to 30 mg/kg, 3 to 4 times. For treatment of Legionnaires' disease, adult: 0.5 to 1.0 g once, 4 times a day. For prevention of recurrence of rheumatic fever, 0.25 g once, 2 times a day. For prevention for infective endocarditis, oral 1 g in 1 hour before surgery, and 0.5 g in 6 hours after surgery. For an animal of 10 to 70 kg body weight, under normal circumstances 50 to 500 mg/day, once every 6-8 hours, orally administered.

Advantageous Effects

It has been surprisingly found that the erythromycin ethylsuccinate hydrate obtained in the present invention can preserve more stable. Erythromycin ethylsuccinate containing crystalline water differs from erythromycin ethylsuccinate anhydride which is easier to absorb moisture. Erythromycin ethylsuccinate containing crystalline water has good storage stability at room temperature, easy storage and transport, and can be conveniently used for the preparation of pharmaceutical formulations. The result of moisture determination by Karl Fischer method is consistent with the result of thermogram. Erythromycin ethylsuccinate 0.25 $H_2O$ and 0.5 $H_2O$ hydrate is found in thermogram.

The erythromycin ethylsuccinate crystalline hydrate according to the present invention was stable during storage. The above sample was sealed in vials and subjected to accelerated stability test at 30° C. using HPLC ($C_{18}$ reverse phase column, 4.6×250 mm, 5 μm), mobile phase: 10 mmol/L sodium dodecyl sulfate solution containing 0.1% triethylamine (pH adjusted to 3.4 with phosphoric acid)—acetonitrile (55:45), detection wavelength was 205 nm, and the flow rate is 1.0 ml/min, and the change of relevant substances and content was detected. It has been surprisingly found that the content of erythromycin ethylsuccinate hydrate and related substances of the present invention did not change significantly. According to CP2005, 5 grams of the sample of the present invention was, at 25° C., placed in a relative humidity of 70% in the test for hygroscopicity. It is surprising that erythromycin ethylsuccinate hydrate leads to less hygroscopic weight gain. Erythromycin ethylsuccinate hydrate according to the present invention exhibits lower hygroscopicity as compared with Erythromycin Ethylsuccinate anhydride, i.e., has higher hygroscopic stability, which benefits package storage, or is more stable storage form than the anhydride. In addition, the deliquescence of anhydride makes it necessary to isolate from air during processing to prevent adhesions, while the hydrate has good sliding properties, thereby improving the operability of the formulation. The results are shown in Table 1 below.

The crystalline solid has higher chemical stability and physical stability than amorphous form and low crystalline form, and exhibits improved moisture absorption, bulk performance and fluidity.

Discoveries to new pharmaceutically useful polymorph compounds provide a new opportunity to improve action characteristics of a medicinal product, and for the formulation scientists they expand the library of materials obtained, for example, by designing a formulation containing a medicine having a target release profile or other desirable characteristics. Tigecycline crystal hydrates or polymorphs are needed in the art.

TABLE 1

Hygroscopicity test result of erythromycin ethylsuccinate hydrate (RH 70% 25° C.)

| Sampling time (48 h) | hygroscopic weight gain %, compared to 0 h |
|---|---|
| Erythromycin Ethylsuccinate 0.5-$H_2O$ hydrate | 0.2% |
| Erythromycin ethylsuccinate 0.25 $H_2O$ hydrate | 0.59% |
| Erythromycin Ethylsuccinate Anhydride | 1.14% |

BEST MODE

All the numerical values used in the specification and claims, apart from those in the examples and other special indications, should be understood to be modified with term 'about' in all the examples. Therefore, unless there are contrary instructions, the numerical parameters given in the present specification and claims are approximations, which may vary with the desired properties sought in the content disclosed in the present invention, equivalent to at least, and is not intended to limit the application of the scope of the claims, each numerical parameter should be explained by considering the number of significant digits and conventional rounding method.

Although the numerical ranges and parameters in broad scope defined in the present invention are approximations, the numerical values provided in the specific examples are reported as precisely as possible. Any numerical value substantially contains some errors necessarily generated from the standard deviation found in their respective test.

It should be noted, unless other definite indications in the context, the singular forms 'a', 'an' and 'the' used in the specification and claims include plural forms of the object; therefore, for example, 'a composition comprising a compound' includes a mixture of two or more compounds. In addition, it should be noted that the term 'or' normally includes 'and/or', unless explicitly stated otherwise in the context.

As used herein, the term 'obtain' refers to a compound with value purity level obtained by isolation. The purity level includes, but not limited to purity level of greater than 90%, 95%, 96%, 97%, 98% and 99%. The purity level can be determined by HPLC.

Pharmaceutical Compositions

The term 'pharmaceutical composition' used in the context means a composition of drug. Said pharmaceutical composition may contain at least one pharmaceutically acceptable carrier.

As used herein, "pharmaceutically acceptable excipient' means a pharmaceutically acceptable carrier or vehicle suitable for the administration of compounds provided in the present invention, including any carrier suitable for particular administration manner known in the art, e.g., solutions or suspensions for parenteral, intradermal, subcutaneous, or topical application can include a sterile diluent (e.g., water for injection, saline solution, a non-volatile oil, and the like); synthetic fat solvent (e.g., polyethylene glycols, glycerine, propylene glycol, etc.); antibacterial agents (e.g., benzyl alcohol, methylparaben, ethylparaben, etc.); antioxidants (e.g., ascorbic acid, sodium bissulfite, etc.); chelating agent (i.e., EDTA, etc.); buffer agent (phosphate, citrate, etc.); and/or osmotic pressure regulating substance (e.g., sodium chloride, glucose, etc.), or their mixture. For further examples, for intravenous administration, the appropriate carriers include normal saline, phosphate buffer and the solution containing the thickener, for example, glucose, polyethylene glycol, etc., as well as their mixtures.

As non-limiting examples, erythromycin ethylsuccinate crystalline hydrate may be optionally mixed with one or more pharmaceutically acceptable excipients, and can be orally administered in following forms: tablets, capsules, dispersible powders, granules, or suspensions containing, e.g. about 0.05 to 5% suspending agent, syrups containing, for example, about 10-50% sucrose, preparations containing, for example, about 20-50% of ethanol; or sterile solutions or suspensions parenterally administered, said suspensions containing 0.05 to 5% of suspending agent in isotonic medium. These pharmaceutical preparations may contain, e.g. from about 25% to about 90% of active ingredient and a carrier, more typically containing 5% to 60% (by weight) of active ingredient.

In order to be further appreciated, the following preferred embodiments of the present invention are described with examples, but it should be understood that these descriptions are only for further illustration of the features and advantages of the present invention, not limitation of the claims of the present invention.

The effects of the present invention are described below with the specific embodiments, but the protection scope of the present invention is not limited by the embodiments below.

Thermal Analytic Method

Thermal analysis test conditions: SETARAM company Setsys 16, a sample quantity of about 3 to about 10 mg, temperature elevation rate: 10 K/min, $N_2$ flow rate: 50 ml/min, temperature: room temperature to about 400° C.

Surprisingly, thermogram (TG-DTA or TG-DSC) of characteristic hydrate of the present invention has corresponding endothermic peak at weight loss platform of about 82 to 140° C.

Powder X-Ray Diffraction Method

The powder X-ray diffraction pattern of erythromycin ethylsuccinate crystalline hydrate was measured by using D/MX-III AX-ray diffraction, voltage: 35 kv, current: 30 mA, scanning speed: 10°/min, step size: 0.02°/step; copper target, monochromator: graphite monochromator; wavelength (A): 1.54, diffraction angle 2θ, scanning range 3-60°.

In one embodiment (Example 1), measured by using a powder X-ray diffraction method at a diffraction angle 2θ measurement range (3-60°), the erythromycin ethylsuccinate 0.5 $H_2O$ hydrate of the present invention has corresponding characteristic values at the position of following 2θ values: about 5.02, 6.42, 6.74, 8.03, 9.01, 10.36, 10.95, 12.82, 13.49, 15.11, 15.94, 16.90, 17.80, 18.22, 18.72, 19.13, 19.78, 20.67, and 23.66.

In one embodiment (Example 2), measured by using a powder X-ray diffraction method at diffraction angle 2θ measurement range (3-60°), the erythromycin ethylsuccinate 0.5 $H_2O$ hydrate of the present invention has corresponding characteristic values at the position of following 2θ values: about 5.04, 6.43, 6.75, 8.00, 9.03, 10.01, 10.35, 10.93, 13.51, 15.12, 15.97, 16.92, 19.19, 19.69, 20.65, 22.42, 23.77, 25.97, 28.66, 29.45.

In one embodiment (Example 3), measured by using a powder X-ray diffraction method at diffraction angle 2θ measurement range (3-60°), the erythromycin ethylsuccinate 0.25 $H_2O$ hydrate of the present invention has corresponding characteristic values at the position of following 2θ values: about 5.04, 6.41, 6.76, 8.01, 9.02, 10.36, 10.94, 12.95, 13.48, 15.10, 15.96, 16.90, 18.23, 19.12, 19.75, 20.64, 21.20, 22.36, 23.78, 24.39, 25.94, 28.63.

MODE FOR INVENTION

Example 1

The Preparation of Erythromycin Ethylsuccinate 0.5 $H_2O$ Hydrate

Figure 1:
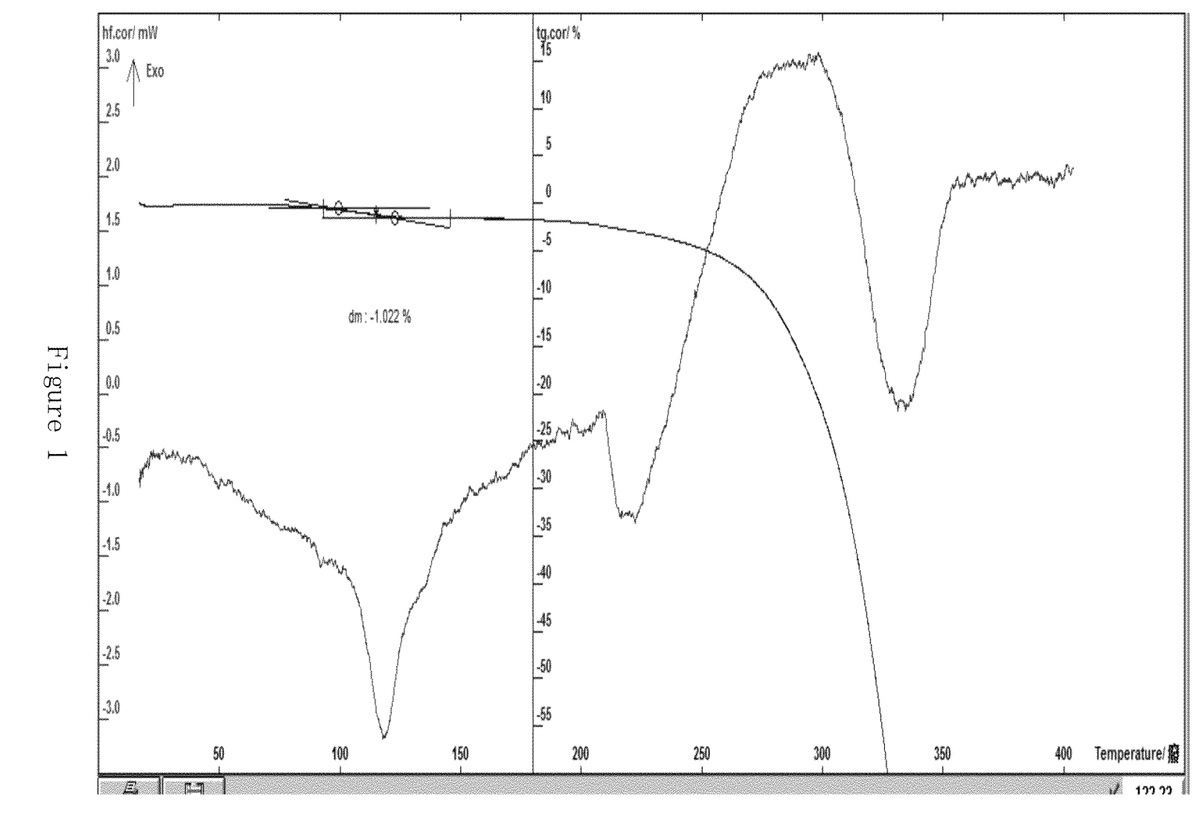
FIG. 1 is thermal analytic pattern of erythromycin ethylsuccinate 0.5 $H_2O$ hydrate.
Figure 2:
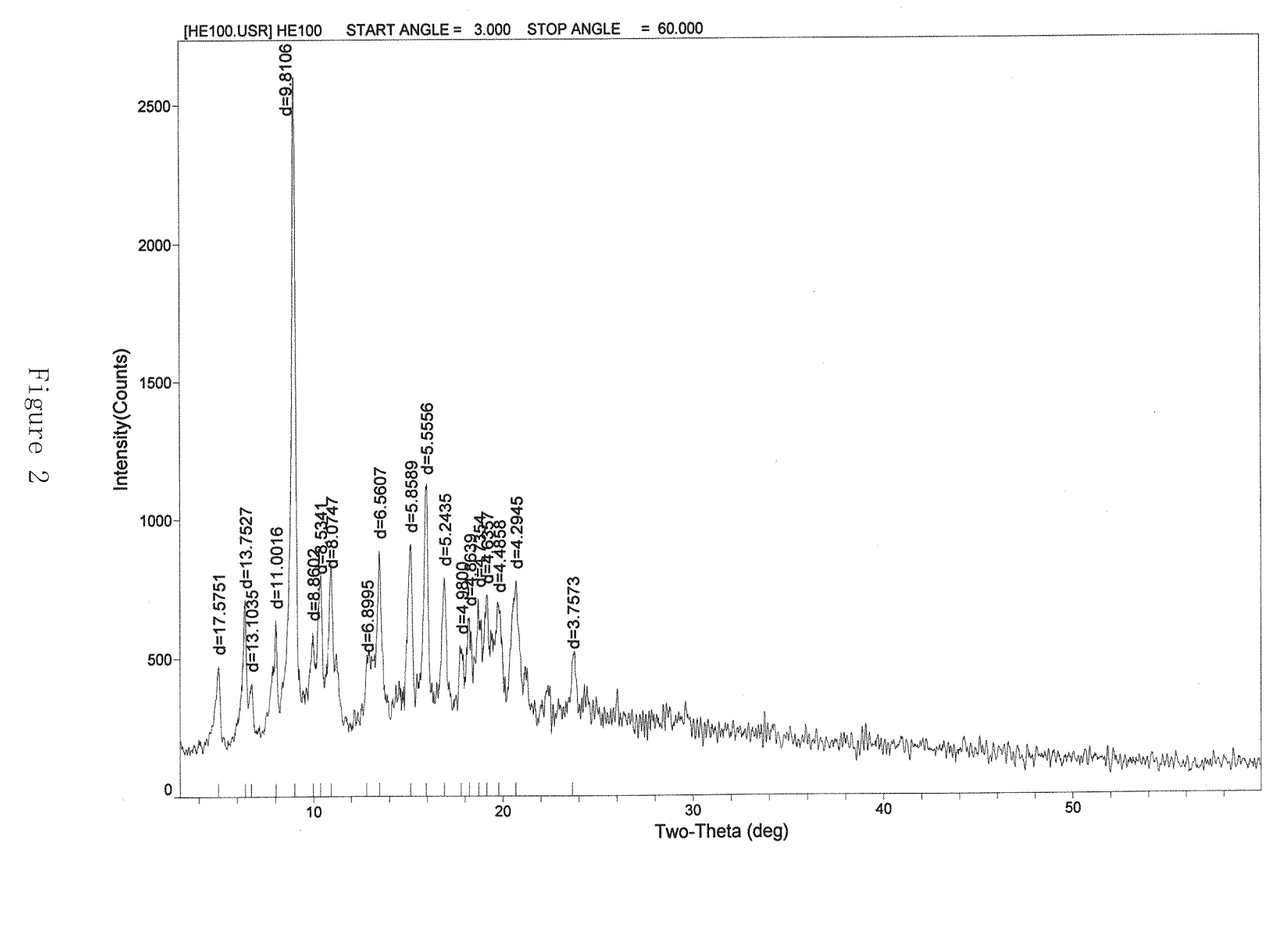
FIG. 2 is powder X-ray diffraction pattern of erythromycin ethylsuccinate 0.5 $H_2O$ hydrate.

To a three-necked flask were added 35 ml of tetrahydrofuran, 10 ml of acetone, 8 g of erythromycin, 15 ml of 47% potassium carbonate, and 10 ml of water, stirred, cooled to 15° C. or below, added 4.8 g of monoethyl succinate chloride, monitored by TLC until the reaction was complete, added slowly 5M aqueous sodium phosphate solution, stirred to control the pH value at about 7.0-8.5; the organic phase was precipitated and separated; to the organic phase was added slowly about 60 ml of water with stirring, cooled to −15-0° C., after the solid was precipitated completely, filtered, the resulting solid was recrystallized with ethanol and water, cooled to about −10° C. After the solid was precipitated completely, and suction filtered, the resulting solid was dried at about 50° C. for 8 h to obtain 4.2 g of white-like solid; melting point: 109.2-111.7° C. (uncorrected). The sample was identified according to items (1) and (2) of erythromycin ethylsuccinate of Chinese Pharmacopoeia CP2005 version, the results comply with corresponding provisions;

Determined by Cartesian method, moisture content was 1.34% (theoretical 1.03%), TG: weight loss of about 1.02% (see FIG. 1), X-ray powder diffraction pattern, see FIG. 2; infrared spectrum: $V^{KBr}_{max}$ cm$^{-1}$ 3452, 2975, 2940, 2886, 2831, 2785, 1738, 1697, 1463, 1377, 1348, 1257, 1169, 1109, 1080, 1054, 1008, 896, 835, 698; MS (ESI) m/z: 862; Elemental Analysis Found: C, 59.37; H, 8.86; N, 1.54. Calculated: C, 59.29; H, 8.79; N, 1.61.

Example 2

Preparation of Erythromycin Ethylsuccinate 0.5-Hydrate

To a three-necked flask were added 40 ml of acetone, 50 ml of tetrahydrofuran, 20 g of erythromycin thiocyanate, stirred at 30-45° C., added 40 ml of 12 g potassium carbonate aqueous solution, stirred for 1 hour, added dropwise 4M aqueous sodium dihydrogen phosphate solution, stirred to control the pH value at about 7.0-8.5; the organic phase was precipitated and separated; to the organic phase was added 40 ml of 47% potassium carbonate and 10 ml water, stirred, cooled to 15° C. or below, added 10 g of monoethyl succinate chloride, monitored by using TLC until the reaction was complete; added dropwise 5M aqueous sodium citrate solution, stirred to control the pH value at about 7.0-8.5; the organic phase was precipitated and separated; to the organic phase was added slowly about 100 ml of water with stirring, cooled to −15-0° C., after the solid was precipitated completely, suction filtered, the resulting solid was recrystallized with isopropanol and water, suction filtered, dried under vacuum of about 0.09 MPa and at about 40° C. for about 4 h to obtain 10.6 g of white-like crystal; melting point: 110-113° C. (uncorrected). The sample was identified according to items (1) and (2) of erythromycin ethylsuccinate of Chinese Pharmacopoeia CP2005 version, the results comply with corresponding provisions; moisture content (determined by Cartesian method): 1.26% (theoretical 1.03%), TG: weight loss of about 1.02% (see FIG. 2), MS (ESI) m/z: 862; Elemental Analysis Found: C, 59.22; H, 8.86; N, 1.54. Calculated: C, 59.29; H, 8.79; N, 1.61.

Example 3

Preparation of Erythromycin Ethylsuccinate 0.25 $H_2O$ Hydrate

Figure 3:
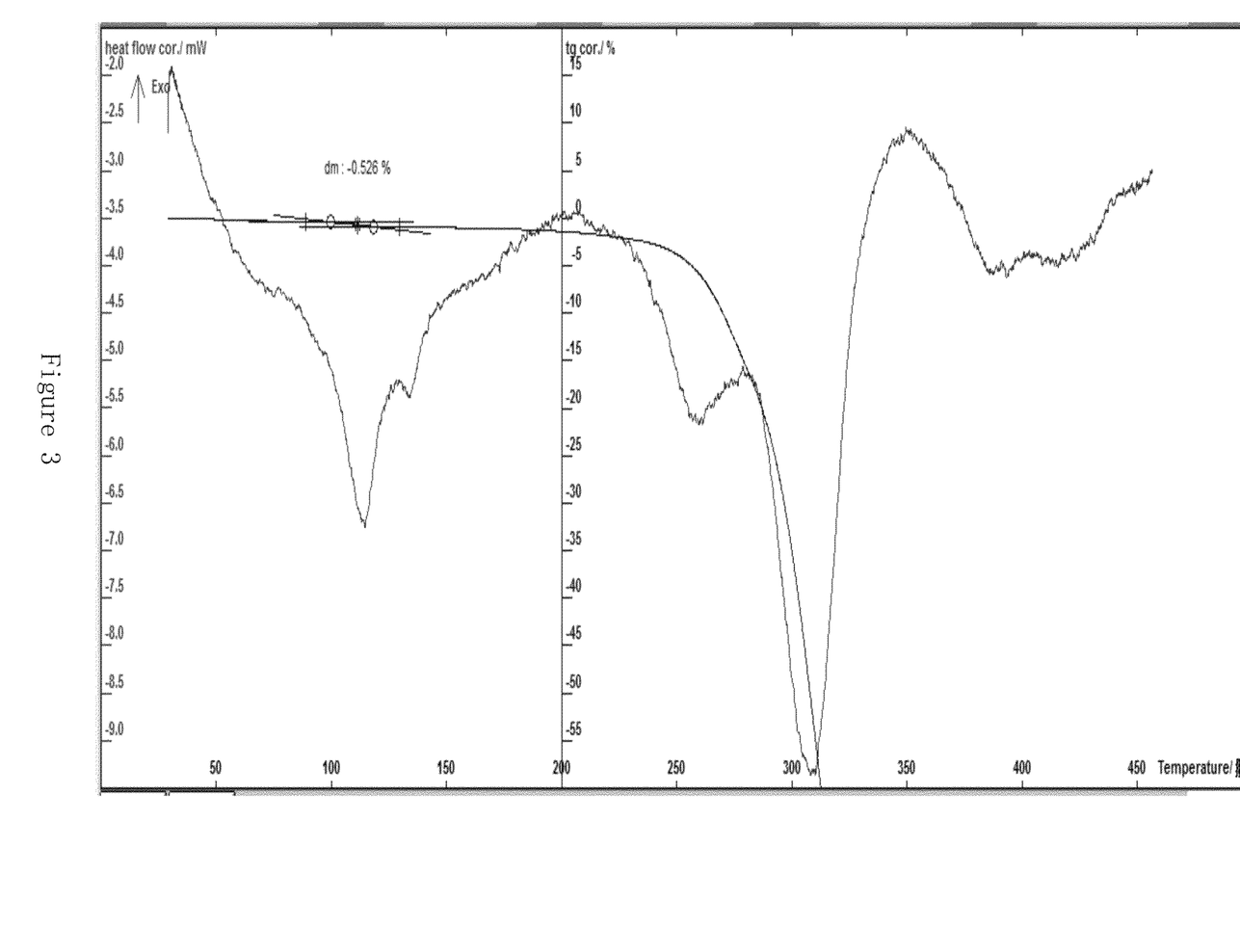
FIG. 3 is thermal analytic pattern of erythromycin ethylsuccinate 0.25 $H_2O$ hydrate.
Figure 4:
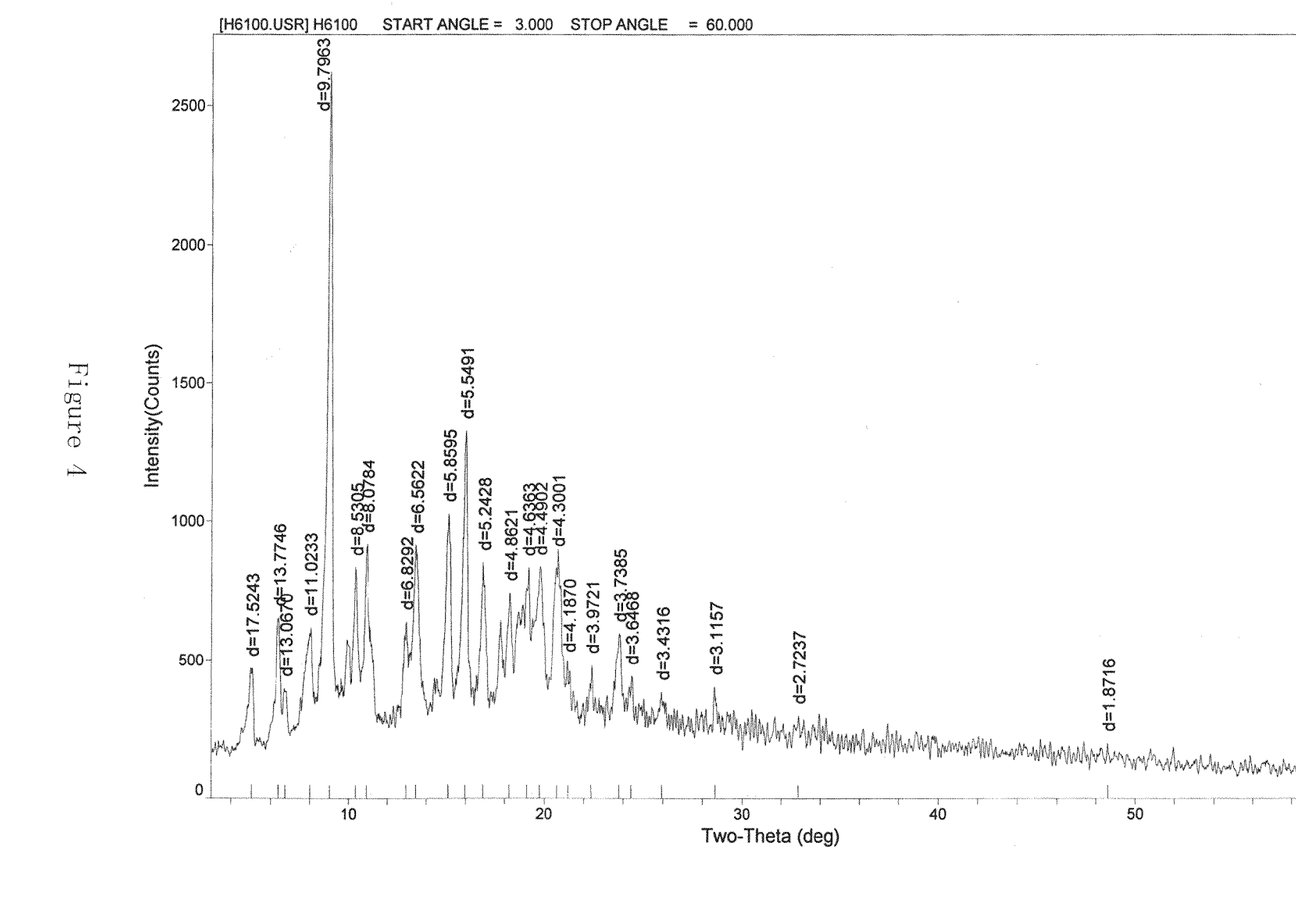
FIG. 4 is powder X-ray diffraction pattern of erythromycin ethylsuccinate 0.25 $H_2O$ hydrate.

At room temperature, to a 500 ml three-necked flask was added 10 g of erythromycin ethylsuccinate 0.5 $H_2O$ hydrate, and then acetone to make the former dissolve completely, added slowly 50-70 ml of purified water with stirring, cooled to −10-4° C., stood to precipitate, filtered, the solid was washed with water, filtered to obtain white-like solid, recrystallized with acetone and water, suction filtered, and dried under vacuum of about 0.09 MPa and at about 60° C. for about 16 h to obtain 6.7 g of white-like crystal; melting point: 109-113° C. (uncorrected); the sample was identified according to items (1) and (2) of erythromycin ethylsuccinate of Chinese Pharmacopoeia CP2005 version, the results comply with corresponding provisions; moisture content (determined by Cartesian method): 0.68% (theoretical value 0.52%), TG: weight loss of about 0.53% (see FIG. 3), falling in the error range of the sample containing 0.25 crystal water, X-ray powder diffraction pattern: see FIG. 4; Infrared spectrum: $V^{KBr}_{max}$ cm$^{-1}$ 3455, 2975, 2940, 2884, 2832, 2785, 1738, 1697, 1462, 1377, 1348, 1257, 1169, 1109, 1080, 1055, 1008, 896, 836, 698; MS (ESI) m/z: 862; Elemental Analysis Found: C, 59.51; H, 8.91; N, 1.52. Calculated: C, 59.60; H, 8.78; N, 1.62.

Example 4

Preparation of Erythromycin Ethylsuccinate 0.25 $H_2O$ Hydrate

To a three-necked flask were added 50 ml of acetone, 36 ml of tetrahydrofuran, 20 g of erythromycin thiocyanate, stirred at 30-45° C., added about 40 ml of 12 g potassium carbonate aqueous solution, stirred for 1 hour, added dropwise 4M aqueous sodium dihydrogen phosphate solution, stirred to control the pH value at about 7.0-8.5; the organic phase was precipitated and separated; to the organic phase was added 40 ml of 47% potassium carbonate and 10 ml water, stirred, cooled to 15° C. or below, added 10 g of monoethyl succinate chloride, monitored by using TLC until the reaction was complete; added dropwise 3M aqueous sodium citrate solution, stirred to control the pH value at about 7.0-8.5; the organic phase was precipitated and separated, to the organic phase was added slowly about 100 ml of water, cooled to −15-4° C., after the solid was precipitated completely, suction filtered, the resulting solid was recrystallized with appropriate amount of isopropanol, acetone and water, suction filtered, dried under vacuum of about 0.09 MPa and at about 58° C. for about 32 h to obtain 9.2 g of white-like crystal; melting point: 110-112.8° C. (uncorrected). The sample was identified according to items (1) and (2) of erythromycin ethylsuccinate of Chinese Pharmacopoeia CP2005 version, the results comply with corresponding provisions; moisture content (determined by Cartesian method): 0.76%, TG: weight loss of about 0.65% (theoretical value 0.52%).

Example 5

Preparation of Erythromycin Ethylsuccinate 0.5 $H_2O$ Hydrate

The solid was prepared according the feeding amount and method described in Example 1: after the solid was precipitated completely, filtered, the resulting solid was recrystallized with an appropriate amount of ethanol, acetone and water, cooled to about 0° C. or below; after the solid was precipitated completely, suction filtered, the resulting solid was dried at about 50° C. for 8 h to obtain 3.8 g of white-like solid; melting point: 109.0-111.8° C. (uncorrected), the sample was identified according to items (1) and (2) of erythromycin ethylsuccinate of Chinese Pharmacopoeia CP2005 version, the results comply with corresponding provisions; moisture content (determined by Cartesian method): 1.28% (theoretical value: 1.03%), TG: weight loss of about 1.02%.

Example 6

Erythromycin Ethylsuccinate Crystalline Hydrates Tablets (250 mg/Tablet, Based on Erythromycin)

Formulation:
erythromycin ethylsuccinate crystalline hydrate: 250 g (based on erythromycin)
Microcrystalline cellulose: 250 g
Sodium carboxymethyl starch: 20 g
Aspartame: 2 g
Polyvinylpyrrolidone 5%: appropriate amount
Magnesium stearate: 2 g Erythromycin ethylsuccinate 0.5 $H_2O$ hydrate or erythromycin ethylsuccinate 0.25 $H_2O$ hydrate (prepared by the method described in Example 1 or Example 2 or Example 3), microcrystalline cellulose, sodium carboxymethyl starch, and aspartame was screened through 100 mesh sieve, and prepared into soft material with an appropriate amount of 5% polyvinyl pyrrolidone, granulated through 18-24 mesh sieve, dried, passed through 14-20 mesh sieve, added micronized silica gel and magnesium stearate, mixed and compacted into tablets.

Example 7

Erythromycin Ethylsuccinate Hydrate Capsules (125 mg/Granule, Based on Erythromycin)

Formulation: erythromycin ethylsuccinate hydrate: 125 g (based on erythromycin)
microcrystalline cellulose: 100 g
Lactose: 20 g
Gelatinised starch 10%: appropriate amount
Magnesium stearate: 2 g Erythromycin ethylsuccinate hydrate (prepared by the method described in Example 1 or Example 2 or Example 3), microcrystalline cellulose, lactose were passed through 100 mesh sieve, prepared into soft material with an appropriate amount of 10% gelatinized starch, granulated through 24-30 mesh sieve, dried, passed through 24-30 mesh sieve, added magnesium stearate, mixed and encapsulated. Or Erythromycin ethylsuccinate hydrate was mixed with an appropriate amount of starch or microcrystalline cellulose, and then directly encapsulated.

Example 8

Erythromycin Ethylsuccinate Hydrate Granules Including Erythromycin Ethylsuccinate 0.5 H₂O Hydrate or Erythromycin Ethylsuccinate 0.25 H₂O Hydrate Granules (125 mg/Package, Based on Erythromycin)

Formulation:
erythromycin ethylsuccinate hydrate: 125 g (based on erythromycin)
Mannitol: 100 g
Lactose: 20 g
Sodium cyclamate: 2 g
Solid edible essence: 1 g
Polyvinylpyrrolidone 5%: appropriate amount Erythromycin ethylsuccinate hydrate (prepared by the method described in Example 1 or Example 2 or Example 3), mannitol, lactose, sodium cyclamate, edible essence were passed through 100 mesh sieve, prepared into soft material with an appropriate amount of 5% polyvinyl pyrrolidone, granulated through 18-24 mesh sieve, dried at 50° C. or below, passed through 14-24 mesh sieve, and packaged.

Example 9

Erythromycin Ethylsuccinate Hydrate Suppositories (250 mg/Granulate, Based on Erythromycin)

Formulation:
Erythromycin ethylsuccinate hydrates 25 g (based on erythromycin, 100 particles feeding)
Polyethylene glycol 4000: 200 g
glycerol: 5 ml
Poloxamer: 70 g
Tween 80: 1 ml Erythromycin ethylsuccinate hydrate (prepared by the method described in Example 1 or Example 2 or Example 3), glycerin, polyethylene glycol 4000, poloxamer, and Tween 80 were mixed, heated in water bath, stirred until the mixture was melted, stirred until the melt was uniform, and then poured rapidly into a suppository mold coated with a lubricant to slightly overflow from suppository mold, cooled and leveled, and drawn.

Example 10

Erythromycin Ethylsuccinate Hydrate Gel

Formulation
Erythromycin ethylsuccinate hydrate 25 g (based on erythromycin, feeding)
Propylene glycol: 10 g
Triethanolamine: 1 g
Glycerol: 10 ml
Carbomer 934: 20 g
Carbomer 1342: 5 g
Lactic acid 1M or sodium hydroxide 1M: appropriate amount
Water to 1000 g Carbomer 934 and Carbomer 1342 were dispersed with water, to the mixture was added glycerin, propylene glycol, triethanolamine, mixed with stirring, added erythromycin ethylsuccinate hydrate (prepared by the method described in Example 1 or Example 2 or Example 3), heated in water bath, stirred, the pH value was adjusted to 5-7 with 1M hydrochloric acid or 1M sodium hydroxide, stirred until uniform, and degassed under vacuum.

It can be understood from professional point of view that the variation of many details is possible, which does not limit the scope and spirit of the present invention. The present invention is not limited to the above examples.

The invention claimed is:

1. An erythromycin ethylsuccinate crystalline hydrate of a general formula of $C_{43}H_{75}NO_{16} \cdot nH_2O$, n=0.25 or 0.5.

2. A composition comprising the erythromycin ethylsuccinate crystalline hydrate according to claim 1.

3. The composition of claim 2, wherein the composition is a solid preparation, ointment or gel for transdermal or transmucosal administration, or a suppository.

4. The composition of claim 2, wherein the composition is a medicament for the treatment or prevention of infection in humans and animals caused by sensitive bacteria, *mycoplasma*, *Chlamydia* or combinations thereof.

5. A process for the preparation of the erythromycin ethylsuccinate crystalline hydrate according to claim 1, the process comprising:
   adding erythromycin to a solvent and stirring at a temperature of 0-50° C., thereby forming a solution, wherein the solvent is one or more of a $C_1$-$C_6$ lower alcohol, a $C_2$-$C_6$ lower nitrile, a $C_3$-$C_8$ lower ketone or $C_2$-$C_8$ lower ether;
   adding sodium bicarbonate, sodium carbonate or potassium carbonate, and water to the solution, stirring, and cooling to 20° C. or below, thereby forming a cooled mixture;
   adding monoethyl succinate halide to the cooled mixture and allowing to react, thereby forming a resultant;
   adding an acid or a base to the resultant to control the pH value at about 7.0-8.5;
   precipitating and separating an organic phase;
   adding water to the organic phase and cooling to −20° C.-10° C.;
   filtering;
   recrystallizing the organic phase with water and a recrystallization solvent one or more times, wherein the recrystallization solvent is one or more of a $C_1$-$C_6$ lower alcohol, a $C_2$-$C_6$ lower nitrile, a $C_2$-$C_8$ lower ether, a $C_3$-$C_8$ lower ketone or $C_1$-$C_6$ lower halogenated hydrocarbons;
   cooling the recrystallized organic phase to −20° C.-10° C.;
   filtering; and
   drying to obtain erythromycin ethylsuccinate crystalline hydrate.

6. The process for the preparation of the erythromycin ethylsuccinate crystalline hydrate according to claim 5, wherein the recrystallization solvent is selected from the group consisting of water, ethanol, isopropanol, acetonitrile, diethyl ether, tetrahydrofuran, acetone, methylene chloride, and ethyl acetate.

7. The process for the preparation of the erythromycin ethylsuccinate crystalline hydrate according to claim 5, wherein the monoethyl succinate halide is monoethyl succinate chloride or monoethyl succinate bromide.

8. A process for the preparation of the erythromycin ethylsuccinate crystalline hydrate according to claim 1, the process comprising:
- adding one or more of erythromycin thiocyanate, erythromycin thiocyanate hydrate, or erythromycin lactate to a solvent and stirring, wherein the solvent is one or more of a $C_1$-$C_6$ lower alcohol, a $C_2$-$C_6$ lower nitrile, a $C_3$-$C_8$ lower ketone or $C_2$-$C_8$ lower ether;
- adding sodium bicarbonate, sodium carbonate or potassium carbonate, and water, and allowing to react with stirring for 1-3 hours;
- adding dropwise an aqueous solution of an acid or a base and stirring to control the pH value at about 7.0-8.5;
- precipitating and separating an organic phase;
- adding sodium bicarbonate, sodium carbonate or potassium carbonate, and water to the organic phase, stirring, and cooling to 20° C. or below;
- adding monoethyl succinate halide and allowing to react, thereby forming a resultant;
- adding an acid or a base to the resultant to control the pH value at about 7.0-8.5;
- precipitating and separating an organic phase;
- adding water to the organic phase and cooling to −20° C.-10° C.;
- filtering;
- recrystallizing the organic phase with water and a recrystallization solvent one or more times, wherein the recrystallization solvent is one or more of a $C_1$-$C_6$ lower alcohol, a $C_2$-$C_6$ lower nitrile, a $C_2$-$C_8$ lower ether, a $C_3$-$C_8$ lower ketone or $C_1$-$C_6$ lower halogenated hydrocarbons;
- cooling the recrystallized organic phase to −20° C.-10° C.;
- filtering; and
- drying to obtain erythromycin ethylsuccinate crystalline hydrate.

9. The process for the preparation of the erythromycin ethylsuccinate crystalline hydrate according to claim 8, wherein the recrystallization solvent is selected from the group consisting of water, ethanol, isopropanol, acetonitrile, diethyl ether, tetrahydrofuran, acetone, methylene chloride, and ethyl acetate.

10. The process for the preparation of the erythromycin ethylsuccinate crystalline hydrate according to claim 8, wherein the monoethyl succinate halide is monoethyl succinate chloride or monoethyl succinate bromide.

11. The composition of claim 4, wherein the composition is a medicament for the treatment or prevention of acute tonsillitis, acute pharyngitis, sinusitis, scarlet fever, cellulitis, diphtheria, diphtheria carriers, gas gangrene, anthrax, tetanus, actinomycosis, syphilis, listeriosis, Legionnaires' disease, *Mycoplasma pneumoniae* pneumonia, *Chlamydia pneumoniae* pneumonia, genitourinary infection caused by *Chlamydia, Mycoplasma, Chlamydia trachomatis* conjunctivitis, oral infection caused by anaerobic bacteria, *Campylobacter jejuni* enteritis, whooping cough, recurrence of rheumatic fever, or infective endocarditis.

* * * * *